United States Patent [19]

Merz

[11] 4,151,355

[45] Apr. 24, 1979

[54] PROCESS FOR THE PREPARATION OF 6-TERT.-BUTYL-3-MERCAPTO-4-AMINO-1,2,4-TRIAZIN-5(4H)-ONE

[75] Inventor: Walter Merz, Leverkusen, Fed. Rep. of Germany

[73] Assignee: Bayer Aktiengesellschaft, Leverkusen, Fed. Rep. of Germany

[21] Appl. No.: 904,072

[22] Filed: May 8, 1978

Related U.S. Application Data

[62] Division of Ser. No. 640,830, Dec. 15, 1975, Pat. No. 4,113,767.

[30] Foreign Application Priority Data

Dec. 21, 1974 [DE] Fed. Rep. of Germany ....... 2460889

[51] Int. Cl.$^2$ ........................................... C07D 253/06
[52] U.S. Cl. ................................................... 544/182
[58] Field of Search ......................................... 544/182

[56] References Cited

U.S. PATENT DOCUMENTS

| | | | |
|---|---|---|---|
| 4,058,526 | 11/1977 | Merz et al. | 544/182 |
| 4,113,767 | 9/1978 | Merz | 544/182 |

FOREIGN PATENT DOCUMENTS 2460889 12/1974 Fed. Rep. of Germany ........... 544/182

*Primary Examiner*—John M. Ford
*Attorney, Agent, or Firm*—Sprung, Felfe, Horn, Lynch & Kramer

[57] ABSTRACT

6-Tert.-butyl-3-mercapto-4-amino-1,2,4-triazin-(4H)-one is prepared by reacting pinacolone with a sulfur chloride at 0° to 80° C., optionally reacting the mixture with an aqueous amine solution, hydrolyzing the resulting product with an alkali metal hydroxide, heating the resulting mixture from 2 to 10 hours at 80° to 150° C., liberating a 3,3-dimethyl-2-oxo-butyric acid by acidifying with a mineral acid and reacting an aqueous solution of said 3,3-dimethyl-2-oxo-butyric acid with thiocarbohydrazide to yield the desired product.

28 Claims, No Drawings

PROCESS FOR THE PREPARATION OF 6-TERT.-BUTYL-3-MERCAPTO-4-AMINO-1,2,4-TRIAZIN-5(4H)-ONE

This is a division of Application Ser. No. 640,830, filed Dec. 15, 1975, now U.S. Pat. No. 4,113,767.

The present invention relates to a process for the preparation of 6-tert.-butyl-3-mercapto-4-amino-1,2,4-triazin-5(4H)-one (III). This compound is useful as an intermediate for the synthesis of herbicidally active substances.

It has already been disclosed that 6-alkyl-substituted or 6-aryl-substituted 3-mercapto-4-amino-1,2,4-triazin-5(4H)-ones, for example 6-methyl-3-mercapto-4-amino-1,2,4-triazin-5(4H)-one or 6-phenyl-3-mercapto-4-amino-1,2,4-triazin-5(4H)-one, can be prepared by reacting aliphatic or aromatic α-keto acids with thiocarbohydrazide (see Chem. Berichte 97, 2173–2178 (1964)).

Thus, 6-tert.-butyl-3-mercapto-4-amino-1,2,4-triazin-5(4H)-one (III) is obtained by reacting 3,3-dimethyl-2-oxobutyric acid ("trimethylpyruvic acid") (I) with thiocarbohydrazide (II), thus:

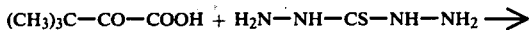

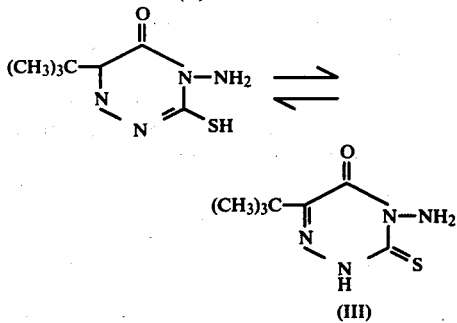

The main technical problem in this systhesis is the preparation of the α-keto acid (I) which is required as a starting material. Most appropriately, this is prepared by oxidizing pinacolone, which has the formula (IV) below, and two methods which can be used industrially are available for this. According to the first method, pinacolone (IV) is oxidized in an aqueous alkaline solution with potassium permanganate and an aqueous solution of the sodium salt of 3,3-dimethyl-2-oxobutyric acid (I) is obtained. Disadvantages of this process are the use of expensive potassium permanganate and the unavoidable formation of manganese dioxide (pyrolucite), the impurities in which make further processing not worthwhile and which has to be deposited on a dump.

According to the second method, pinacolone (IV) is first reacted with elementary chlorine to give dichloropinacolone of the formula (V) below, which on saponification with aqueous metal hydroxide gives the sodium salt of "trimethyl-lactic acid" of the formula (VI). The oxidation of the compound (VI) to give "trimethyl-pyruvic acid" (I) is likewise achieved only with potassium permanganate, but requires only one third of the amount required according to the first method. However, in this case manganese dioxide is again obtained as waste which cannot be utilized. The two methods are represented by the following reaction scheme:

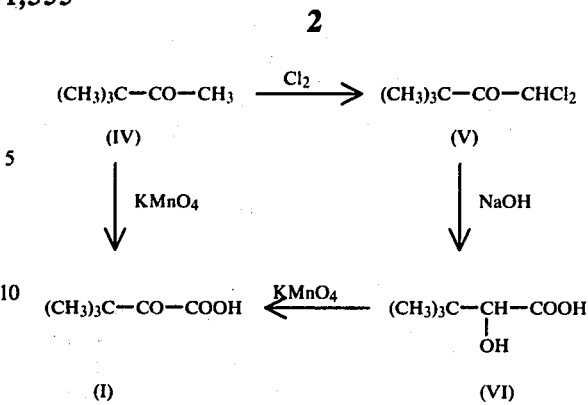

As is also known, salts of α-ketocarboxylic acids of the formula (VIII) below can be obtained when thioamides of the formula (VII) are hydrolyzed by heating with aqueous alkali metal hydroxide (see, for example, J. Amer. Chem. Soc. 78, 4135-9 (1956) according to the following equation:

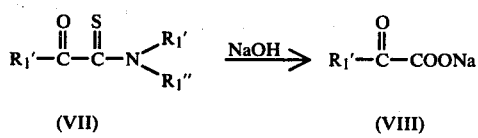

wherein $R_1$, $R_1'$ and $R_1''$ are aliphatic or aromatic hydrocarbon radicals.

However, this method is not suitable for the synthesis of "trimethylpyruvic acid" (I) since no usable process for the preparation of the tert.-butyl-glyoxyl-thioamides of the formula

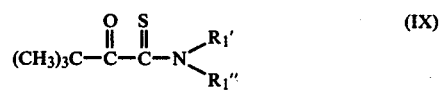

required as starting materials, was known hitherto.

According to a more recent process it is possible to prepare aryl-glyoxyl-thiodimethylamide of the formula (XI) below, by reacting aromatic methylketones (X) with disulfur dichloride ($S_2Cl_2$) and treating the reaction product (a resin of unknown structure), dissolved in dimethylformamide, with dilute aqueous sodium hydroxide solution (see Int. J. Sulfur Chem., A, vol. 2, No. 2, pages 89–92 (1972)). Further, hydrolysis of the α-ketothioamides (XI) by heating with aqueous sodium hydroxide solution gives the sodium salts of the corresponding α-ketocarboxylic acids (VIII a):

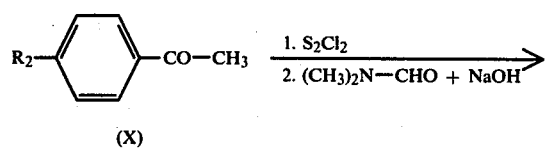

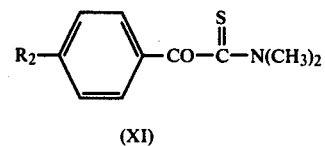

(XI) 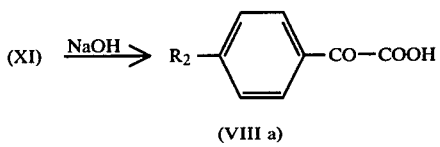 (VIIIa)

wherein

R₂ is hydrogen, methyl, chlorine or methoxy.

Apart from the fact that this process is restricted to aryl alkyl ketones of the type of the compounds (X), the process has various disadvantages: the use of expensive dimethylformamide, which, as both a reactant and the solvent, has to be employed in excess and which cannot be recovered by simple means but would pass into the effluent; the fact that some of the arylglyoxyl-thiodimethylamides (XI) formed are soluble in the reaction mixture and that thus in some cases losses in yield arise; and also that the aryl-glyoxylthiodimethylamides (XI) must be isolated before they can be hydrolyzed to the corresponding α-keto acids.

The present invention provides a process for the preparation of 6-tert.-butyl-3-mercapto-4-amino-1,2,4-triazin-5(4H)-one, which has the formula

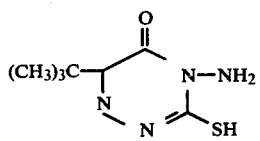 (IIIa), in a "one-pot" reaction in which (1) pinacolone, of the formula $(CH_3)_3C-CO-CH_3$ (IV), is reacted with a sulfur chloride of the formula

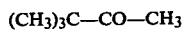 (XII), wherein n is 1 or 2, at a temperature between 0° and 80° C., preferably between 20° and 60° C. (gaseous hydrogen chloride being split off), (2) the reaction mixture is then reacted directly, without further purification, with an aqeuous solution of an amine of the general formula

 (XIII), in which

R and R', which may be identical or different, are each hydrogen, alkyl with 1–8 carbon atoms, cycloalkyl with 5–6 carbon atoms of aryl which has 6–10 carbon atoms and which is optionally substituted by methyl or chlorine, or R and R' conjointly form a radical —(CH₂)ₘ— (where m=4, 5 or 6) or —(CH₂)₂—O—(CH₂)₂—, (3) the tert.-butyl-glyoxyl-thioamide of the formula

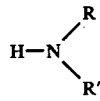 (XIV)

wherein

R and R' have the above-mentioned meaning, which is thus formed (in an exothermic reaction) is hydrolyzed without intermediate isolation by adding at least 2 moles of alkali metal hydroxide per mole of pinacolone (IV) and heating for 2 to 10 hours at 80°–150° C., preferably 100°–130°, to give an alkali metal salt of 3,3-dimethyl-2-oxo-butyric acid of the formula

 (Ia)

wherein

M is an alkali metal, especially sodium or potassium, (4) 3,3-dimethyl-2-oxo-butyric acid (I) is liberated from the salt by acidification with a mineral acid, especially hydrochloric acid or sulfuric acid (the sodium sulfide (Na₂S) and sodium bisulfide (NaHS), previously formed, simultaneously being converted into hydrogen sulfide (H₂S), which escapes as a gas), and (5) the aqueous solution of the acid (I), if appropriate after filtering off any small amount of sulfur which has precipitated on acidification, is reacted, in the customary manner, with thiocarbohydrazide (II).

It is to be regarded as extremely surprising that it is possible, by means of the reaction of pinacolone (IV) with a sulfur chloride of the formula (XII) and the reaction of the reaction product (which is not isolated) with an aqueous solution of an amine (XIII), to prepare, in a technically simple manner and in high yields, tert.-butyl-glyoxyl-thioamides (XIV), which are scarcely accessible by other means and which can then be converted, without isolation, into the desired triazine derivative (III).

According to the state of the art it could not have been expected that reaction of the aliphatic ketone pinacolone with sulfur chlorides of the formula (XII) would give a reaction product which can be reacted with an aqeuous amine and can give tert.-butyl-glyoxyl-thioamides of the formula (XIV). It was merely known that aromatic methyl ketones (X) can be reacted specifically with disulfur dichloride (S₂Cl₂) and that the reaction products can be converted into arylglyoxylthiodimethylamides (XI) only by further reaction with dimethylformamide and dilute sodium hydroxide solution (see T. Matsuda and Y. Takada, Int. J. Sulfur Chem., A, Vol. 2 (1972)). It could not be expected from the set of formulae given by these authors and the structure of the intermediate that it would be possible to react the reaction product of pinacolone and S₂Cl₂ with aqueous amine solutions according to the process of the present invention. Accordingly, it was also not to be expected that it is possible to obtain the same reaction products even with sulfur dichloride (SCl₂) and thus to achieve even better yields, compared with the previously known process.

The process according to the invention has a number of advantages. Thus, expensive potassium permanganate is not required for the oxidation stage and there is no unavoidable formation of manganese dioxide (pyrolucite) which cannot be utilized. The sulfur chlorides to be used according to the invention are simple and cheap to prepare and the by-products obtained, that is to say hydrogen sulfide or the sodium bisulfide solution and elementary sulfur prepared from this, can readily be used in other chemical processes.

A further advantage of the process according to the invention is the ease with which the individual reaction steps can be carried out. Thus, for example, the only stage which is exothermic is the reaction of the reaction product of pinacolone (IV) and the sulfur chloride (XII)

with the aqueous solution of suitable amines (XIII), but the reaction temperature is not critical and can be from 20°–100° C. In contrast, the best prior-art processes have three highly exothermic reaction steps (chlorination, hydrolysis and permanganate oxidation), owing to which the consumption of coolant (energy consumption) is high; moreover, the performance of the reaction is made more difficult by the fact that the temperature has to be kept within very narrow limits.

Furthermore, the tert.-butyl-glyoxyl-thioamides (XIV) can be obtained directly according to the process of the invention by reaction of the reaction product of pinacolone and the sulfur chloride with aqueous solutions of readily accessible amines and therefore the use of dimethylformamide, which is expensive and not readily obtainable, can be avoided.

A further advantage of the process according to the invention is that the amines (XIII) can be recovered after hydrolysis of the tert.-butyl-glyoxyl-thioamides (XIV). If they are low-boiling they distil off and, after absorption in water, can be re-used for the reaction according to the invention. In this way, starting materials are saved and no additional undesirable waste substances are obtained, which would place a burden on the effluent.

If pinacolone, sulfur dichloride, dimethylamine, sodium hydroxide solution and thiocarbohydrazide are used as the starting materials, the course of reaction can be represented by the following set of formulae:

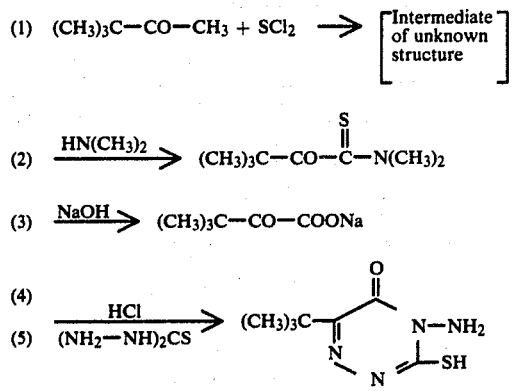

The starting materials to be used according to the invention are known. Examples of amines of the formula (XIII) which may be mentioned are: ammonia, methylamine, ethylamine, propylamine, isopropylamine, butylamine, pentylamine, hexylamine, octylamine, dimethylamine, diethylamine, dipropylamine, dibutylamine, dipentylamine, dihexylamine, dioctylamine, methylethylamine, methylbutylamine, methyloctylamine, cyclohexylamine, dicyclohexylamine, aniline, N-methylaniline, pyrrolidine, piperidine and morpholine.

Further details on the way in which the process according to the invention is carried out are given in the following text.

The first reaction step of the process according to the invention can be carried out in the presence of a diluent which is inert towards sulfur chlorides or without such a diluent. Preferably, carbon tetrachloride, tetrachloroethylene or excess pinacolone is used as the diluent or the reaction is carried out without any solvent. The reaction is carried out at temperatures between 0° and 80° C., preferably between 20° C. and 60° C. It can be carried out under normal pressure, but also under slightly elevated or reduced pressure. In general, the reaction is carried out under atmospheric pressure with a slight excess pressure or reduced pressure of at most 50 mbars, preferably at most 20 mbars. When carrying out the process according to the invention, 0.5 to 2.0 moles of $S_2Cl_2$ or 0.5 to 3.0 moles of $SCl_2$, preferably 1.0–1.2 moles of $S_2Cl_2$ or 1.5–2.0 moles of $SCl_2$, are employed per mole of pinacolone. According to a particular embodiment, it is also possible to carry out this first reaction step continuously.

The second reaction step of the process according to the invention can be carried out in the presence of a diluent which is inert towards sulfur chlorides or without such a diluent. Preferably, carbon tetrachloride, tetrachloroethylene or excess pinacolone is used as the diluent, or the reaction is carried out without any diluent. The amines (III) which can be used according to the invention are employed in every case as aqueous solutions and the concentration may be as desired between 1 and 80% by weight, preferably from 20–60% by weight. The reaction is carried out at temperatures of 0°–120° C., preferably 20°–80° C. It can be carried out under normal pressure but also under slightly elevated or reduced pressure. In general, the reaction is carried out at atmospheric pressure with a slight excess pressure or reduced pressure of at most 50 mbars, preferably at most 20 mbars. When carrying out the process according to the invention, 1 to 5 moles, preferably 1.5 to 3.0 moles and especially 2.0 to 2.5 moles, of an amine of the formula (XIII) are employed per mole of pinacolone which has been reacted with sulfur chloride of the formula (XII). According to a particular embodiment it is also possible to carry out this second reaction step continuously.

According to a specific embodiment it is also possible to omit this reaction step completely and to treat the reaction mixture of pinacolone (IV) and sulfur chloride (XII) directly with the aqueous solution of an alkali metal hydroxide. This then also gives "trimethylpyruvic acid" (I), which can be reacted with thiocarbohydrazide (II) to give 6-tert.-butyl-3-mercapto-4-amino-1,2,4-triazin-5(4H)-one (III). The advantage of this embodiment is that no amines are required and one reaction step is saved. However, in this case, the yields of end product (III) are lower.

The third reaction step of the reaction according to the invention can be carried out in the presence of an organic diluent which is stable towards aqueous alkali or without such a diluent and solely with water. Diluents which can be used are preferably solvents which are immiscible with water and which are stable towards alkali, especially hydrocarbons, such as toluene, xylene and chlorobenzene and also ketones, such as methyl isobutyl ketone, pinacolone and cyclohexanone. Preferably, excess pinacolone is used as the diluent or the reaction is carried out without any diluent. The alkali metal hydroxides which can be used according to the invention can be sodium hydroxide or potassium hydroxide, preferably sodium hydroxide. The reaction is carried out at temperatures of 80°–150° C., preferably at 100°–130° C. and especially at 110°–120° C. It can be carried out not only under normal pressure and slightly reduced pressure but also under elevated pressure. In general, the reaction is carried out under atmospheric pressure or under slightly reduced pressure of at most 30 mbars or under an excess pressure of at most 10 bars. When carrying out the process according to the invention, 2 to 5 moles, preferably 3.0 to 4.0 moles, of alkali metal hydroxide are employed per mole of tert.-butyl-glyoxyl-thioamide (XIV). According to a particular embodiment it is also possible to carry out this third reaction step continuously.

It is a special feature of the invention that the alkaline treatment can be effected with substantially 2 moles of alkali per mole of thioamide whereas the general practice in reaction of this type was to employ at least 3 and often more moles. With such larger amounts the by-product was sodium sulfide but under the instant conditions the by-product is sodium hydrogen sulfide. Stated alternatively, to balance the reaction equation employing only 2 moles of alkali it is essential that one of the by-products is sodium hydrogen sulfide but in other reactions of this type the reaction proceeds directly to sodium sulfide so that at least 3 moles of alkali are required to permit complete reaction of the starting material. Thus, under the instant conditions sodium hydrogen sulfide forms and is stable. The equations involving 2 and 3 moles of sodium hydroxide are as follows:

$$(CH_3)_3C-CO-\overset{S}{\overset{\|}{C}}-N(CH_3)_2 + 3\ NaOH \longrightarrow$$

$$(CH_3)_3C-CO-COONa + H_2O + HN(CH_3)_2 + Na_2S$$

$$(CH_3)_3C-CO-\overset{S}{\overset{\|}{C}}-N(CH_3)_2 + 2\ NaOH \longrightarrow$$

$$(CH_3)_3C-CO-COONa + HN(CH_3)_2 + NaHS$$

6-Tert.-butyl-3-mercapto-4-amino-1,2,4-triazin-5(4H)-one (III), which can be prepared according to the invention, can be used as an intermediate for the synthesis of herbicidally active substances. For example, 6-tert.-butyl-3-methylthio-4-amino-1,2,4-triazin-5(4H)-one (XV), a compound having a herbicidal action is obtained by S-methylation by means of methyl iodide or methyl bromide (see U.S. Patent No. 3,671,523), thus:

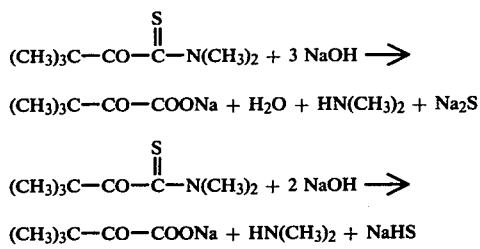

(III)

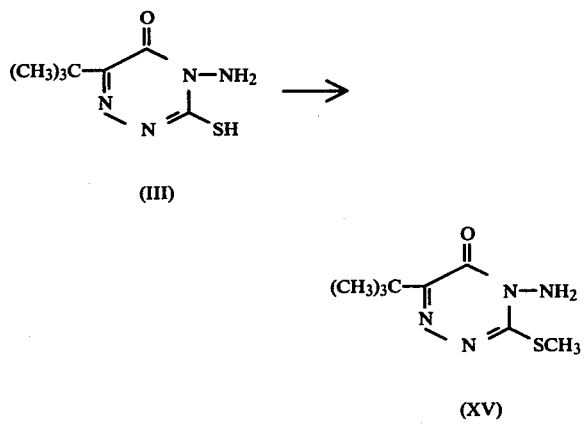

(XV)

4 parts by weight of 3-mercapto-4-amino-6-tert.-butyl-1,2,4-triazin-5-(4H)-one are dissolved in a mixture of 11 parts by weight of 2 normal sodium hydroxide solution and 4 parts by weight of methanol and the solution is treated at 0° C. with 3.2 parts by weight of methyl iodide. The reaction mixture is then stirred at 20° C. for a further 4 hours. The reaction product crystallizes out, is filtered off, dried and recrystallized from benzene. 3.52 parts by weight of 3-methylthio-4-amino-6-tert.-butyl-1,2,4-triazin-5(4H)-one (XV) of melting point 126°–127° are obtained. Yield: 82% of theory.

The process of this invention is illustrated by the following preparative examples.

Preparation of 6-tert.-butyl-3-mercapto-4-amino-1,2,4-triazin-5(4H)-one

EXAMPLE 1

100 g of pinacolone (1 mole) were initially introduced into a stirred flask and 154.5 g (1.5 moles) of sulfur dichloride were added dropwise in the course of 2 hours at 20°–40° C., whilst stirring and cooling slightly, HCl being released via a condenser. After the mixture had been further stirred for 1 hour at 40° C., a solution of 90 g (2 moles) of dimethylamine in water (as an approximately 40% strength solution) was allowed to run in, over the course of about 30 minutes, at 60°–80° C., while cooling with water and the mixture was stirred for a further 30 minutes at the same temperature. A solution of 140 g (3.5 moles) of NaOH in 300 ml of water was then added and the mixture was heated under reflux for 4–6 hours, dimethylamine being released as a gas via the condenser and being absorbed in water. After cooling to 60°–70° C., the pH of the mixture was adjusted to 3.0 with hydrochloric acid (hydrogen sulfide being released as a gas and being absorbed in sodium hydroxide solution) and elemental sulfur, which had precipitated at the same time, was filtered off. 106 g (1.0 mole) of thiocarbohydrazide were added to the clear filtrate and the mixture was reacted at pH 1 and 50°–80° C. to give 6-tert.-butyl-3-mercapto-4-amino-1,2,4-triazin-5(4H)-one. This was very sparingly soluble in the reaction medium and could easily be isolated by filtering off. Yield: 150 g (or 75% of theory).

In the foregoing example the 3.5 moles of NaOH can be replaced by 2 moles and the step run under pressure and substantially similar results obtained.

EXAMPLE 2

According to the instructions in Example 1, 100 g (1.0 mole) of pinacolone were reacted with 206 g of sulfur dichloride (2.0 moles) and the reaction mixture was converted, as described, into 6-tert.-butyl-3-mercapto-4-amino-1,2,4-triazin-5(4H)-one.
Yield: 149 g (or 74.5% of theory).

EXAMPLE 3

According to the instructions in Example 1, 100 g (1.0 mole) of pinacolone were reacted with 135 g (1.0 mole) of disulfur dichloride and the reaction mixture was converted, as described, into 6-tert.-butyl-3-mercapto-4-amino-1,2,4-triazin-5(4H)-one.
Yield: 145 g (or 72.5% of theory).

EXAMPLE 4

According to the instructions in Example 1, 100 g (1.0 mole) of pinacolone were reacted with 175.5 g (1.3 moles) of disulfur dichloride and the reaction mixture was converted, as described, into 6-tert.-butyl-3-mercapto-4-amino-1,2,4-triazin-5(4H)-one.
Yield: 140 g (or 70% of theory).

EXAMPLE 5

154.5 g (1.5 moles) of sulfur dichloride were initially introduced into a stirred flask and 100 g (1.0 mole) of pinacolone were added dropwise in the course of 2 hours at 20°–40° C., whilst stirring and cooling slightly, HCl being released via the reflux condenser. After the reaction mixture had been stirred for a further hour at 40° C., it was added dropwise in the course of 30–60 minutes at 60°–80° C., whilst cooling, to 220 ml of a 40.5% strength solution of 2 moles of dimethylamine in water. A solution of 140 g (3.5 moles) of NaCH in 300 ml of water was then added and the mixture was heated under reflux for 4–6 hours, dimethylamine being released as a gas via the reflux condenser and being absorbed in water. After cooling to 60°–70° C., the pH of the mixture was adjusted to 3.0 with hydrochloric acid, whilst continuing to cool (hydrogen sulfide being released as a gas and being absorbed in sodium hydroxide solution) and elementary sulfur, which had precipitated at the same time, was filtered off. 106 g (1.0 mole) of thiocarbohydrazide were added to the clear filtrate and the mixture was reacted at pH 1 and 50°–80° C. to give 6-tert.-butyl-3-mercapto-4-amino-1,2,4-triazin-5-(4H)-one. This was very sparingly soluble in the reaction mixture and could be isolated easily by filtering off. Yield 150 g (or 75% of theory).

EXAMPLE 6

100 g (1.0 mole) of pinacolone were reacted with 154.5 g (1.5 moles) of sulfur dichloride in the same way as described in Example 1. 370 ml of a 25% strength aqueous ammonia solution were added dropwise to the reaction mixture at a maximum temperature of 60° C., whilst cooling slightly, and the mixture was stirred for a further 30 minutes. After further reaction analogously to Example 1, 66 g of 6-tert.-butyl-3-mercapto-4-amino-1,2,4-triazin-5(4H)-one (33% of theory were obtained.

EXAMPLE 7

154.5 g (1.5 moles) of sulfur dichloride were added dropwise in the course of 2 hours to 100 g (1.0 mole) of pinacolone at 40°–45° C., hydrogen chloride being released as a gas. After stirring the mixture for a further hour at 40° C., a solution of 146 g (2 moles) of diethylamine in 200 ml of water was added dropwise at 60°–80° C. 220 ml of 50% strength sodium hydroxide solution were added and the mixture was heated under reflux for 4 hours and adjusted to pH 3 with hydrochloric acid. 10.9 g of solids (mainly sulfur) and 78 g of an oil separated out. When reacted with thiocarbohydrazide under the conditions described above, the aqueous phase gave 52 g of tert.-butyl-3-mercapto-4-amino-1,2,4-traizin-5(4H)-one (26% of theory). It was not possible to obtain any more of the desired product from the 78 g of oil by renewed hydrolysis.

EXAMPLE 8

174 g (2.0 moles) of morpholine and 200 ml of water were added dropwise at 60°–80° C. to the reaction mixture consisting of 100 g (1.0 mole) of pinacolone and 154.5 g (1.5 moles) of sulfur dichloride. After hydrolyzing with sodium hydroxide solution for 4 hours, acidifying, filtering and reacting with excess thiocarbohydrazide, 100 g (50% of theory) of 6-tert.-butyl-3-mercapto-4-amino-1,2,4-triazin-5(4H)-one were obtained.

EXAMPLE 9

242.5 g (2 moles) of N-ethylaniline were added dropwise in the course of 15 minutes at 80°–100° C. to the reaction mixture consisting of 100 g (1.0 mole) of pinacolone and 154.5 g (1.5 moles) of sulfur dichloride. After alkaline hydrolysis and the above-described working up and reaction with thiocarbohydrazide, 34 g (17% of theory) of 6-tert.-butyl-3-mercapto-4-amino-1,2,4-triazin-5-(4H)-one were obtained.

It will be understood that the specification and examples are illustrative but not limitative of the present invention and that other embodiments within the spirit and scope of the invention will suggest themselves to those skilled in the art.

What is claimed is:

1. A process which comprises
   (1) reacting pinacolone, of the formula

with a sulfur chloride of the general formula

wherein
n is 1 or 2,
at a temperature between 0° and 80° C.,
   (2) reacting the reaction mixture directly, without further purification, with an aqueous solution of an amine of the general formula

in which
R and R' which may be identical or different, are each hydrogen, alkyl of from 1 to 8 carbon atoms, cycloalkyl of from 5 to 6 carbon atoms or aryl of from 6 to 10 carbon atoms and which is optionally substituted by methyl or chlorine, or
R and R' conjointly form a radical —(CH$_2$)$_m$— (where m=4, 5, or 6) or —(CH$_2$)$_2$—O—(CH$_2$)$_2$—,
   (3) hydrolyzing the thus-formed tert.-butyl-glyoxyl-thioamide of the general formula

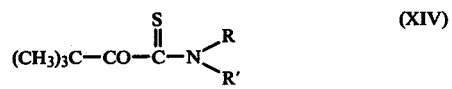

wherein
R and R' identified as above without intermediate isolation by adding at least 2 moles of alkali metal hydroxide of the formula MOH per mole of pinacolone (IV) and heating for from 2 to 10 hours at 80° to 150° C., to give an alkali metal salt of 3,3-dimethyl-2-oxo-butyric acid of the formula

wherein
M is an alkali metal,
   (4) liberating the 3,3-dimethyl-2-oxo-butyric acid of the formula

from the salt (Ia) by acidifying with a mineral acid, and
   (5) reacting the aqueous solution of 3,3-dimethyl-2-oxo-butyric acid, after filtering off any sulfur precipitated on acidifying, with thiocarbohydrazide of the formula

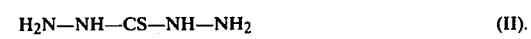

2. A process as claimed in claim 1 wherein step (1) is effected at a temperature of from 20° to 60° C.

3. A process as claimed in claim 1 wherein the sulfur chloride is S₂Cl₂.

4. A process as claimed in claim 1 wherein the sulfur chloride is used in an amount of from 0.5 to 2 moles per mole of pinacolone.

5. A process as claimed in claim 3 wherein the sulfur chloride is used in an amount of from 0.5 to 2 moles per mole of pinacolone.

6. A process as claimed in claim 3 wherein the sulfur chloride is used in an amount of from 1.0 to 1.2 moles per mole of pinacolone.

7. A process as claimed in claim 1 wherein the sulfur chloride is SCl₂.

8. A process as claimed in claim 7 wherein the sulfur chloride is used in an amount of from 0.5 to 3 moles per mole of pinacolone.

9. A process as claimed in claim 7 wherein the sulfur chloride is used in an amount of from 1.5 to 2.0 moles per mole of pinacolone.

10. A process as claimed in claim 1 wherein step (1) is carried out in the presence of a diluent.

11. A process as claimed in claim 10 wherein said diluent is carbon tetrachloride or tetrachloroethylene.

12. A process as claimed in claim 10 wherein said diluent is excess pinacolone.

13. A process as claimed in claim 1 wherein the amine (XIII) as added in step (2) is an aqueous solution having an amine concentration of from 1 to 80% by weight.

14. A process as claimed in claim 13 wherein the amine (XIII) as added in step (2) is an aqueous solution having an amine concentration of 20 to 60% by weight.

15. A process as claimed in claim 1 wherein from 1 to 5 moles of the amine (XIII) are employed per mole of the reacted pinacolone.

16. A process as claimed in claim 15 wherein from 1.5 to 3 moles of the amine (XIII) are employed per mole of the reacted pinacolone.

17. A process as claimed in claim 15 wherein from 2.0 to 3.5 moles of the amine (XIII) are employed per mole of the reacted pinacolone.

18. A process as claimed in claim 1 wherein the amine (XIII) is selected from ammonia, methylamine, ethylamine, propylamine, isopropylamine, butylamine, pentylamine, hexylamine, octylamine, dimethylamine, diethylamine, dipropylamine, dibutylamine dipentylamine, dihexylamine, dioctylamine, methylethylamine, methylbutylamine, methyloctylamine, cyclohexylamine, dicyclohexylamine, aniline, N-methylaniline, pyrrolidine, piperidene and morpholine.

19. A process which comprises
(a) reacting pinacolone, of the formula $(CH_3)_3C—CO—CH_3$     (IV), with a sulfur chloride of the general formula $S_nCl_2$     (XII), wherein
n is 1 or 2, at a temperature between 0° and 80° C.,
(b) hydrolyzing the resulting reaction product without intermediate isolation by adding at least 2 moles of alkali metal hydroxide of the formula MOH per mole of pinacolone (IV) and heating for from 2 to 10 hours at 80° C. to 150° C. to give an alkali metal salt of 3,3-dimethyl-2-oxo-butyric acid of the formula $(CH_3)_3C—CO—COO^{\ominus}M^{\oplus}$     (Ia), wherein
M is an alkali metal,
(c) liberating the 3,3-dimethyl-2-oxo-butyric acid of the formula $(CH_3)_3C—CO—COOH$     (I), from the salt (Ia) by acidifying with a mineral acid, and
(d) reacting the aqueous solution of 3,3-dimethyl-2-oxo-butyric acid, after filtering off any sulfur precipitated on acidifying, with thiocarbohydrazide of the formula $H_2N—NH—CS—NH—NH_2$     (II).

20. A process as claimed in claim 1 wherein from 2 to 5 moles of the alkali metal hydroxide are used, in step (3) per mole of the tert.-butyl-glyoxyl-thioamide (XIV).

21. A process as claimed in claim 20 wherein from 3 to 4 moles of the alkali metal hydroxide are used, in step (3), per mole of the tert.-butyl-glyoxyl-thioamide (XIV).

22. A process as claimed in claim 1 wherein the alkali metal hydroxide is sodium or potassium hydroxide.

23. A process as claimed in claim 1 wherein step (3) is effected at from 100° to 130° C.

24. A process as claimed in claim 23 wherein step (3) is effected at from 110° to 120° C.

25. A process as claimed in claim 1 wherein step (3) is effected in the presence, as a diluent, of water.

26. A process as claimed in claim 1 wherein steps (1), (2), and (3) are effected continuously.

27. A process as claimed in claim 1 wherein the mineral acid in step (4) is hydrochloric acid or sulfuric acid.

28. A process for the preparation of 6-tert.-butyl-3-mercapto-4-amino-1,2,4-triazin-5(4H)-one which process comprises reacting pinacolone with sulfur dichloride at a temperature of from 0° to 80° C., adding an aqueous solution of dimethylamine, adding a solution of an alkali metal hydroxide in an amount to provide at least 2 moles of alkali metal hydroxide per mole of pinacolone, heating the resulting mixture to release dimethylamine, adding a mineral acid and filtering off the precipitating elemental sulfur, adding thiocarbohydrazide to give the desired 6-tert.-butyl-3-mercapto-4-amino-1,2,4-triazine-5(4H)-one.

* * * * *